(12) United States Patent
Pryor et al.

(10) Patent No.: US 10,738,808 B2
(45) Date of Patent: Aug. 11, 2020

(54) COMPACT SUPPORT CLAMP

(71) Applicant: Pryor Products, Inc., Oceanside, CA (US)

(72) Inventors: Paul Pryor, Fallbrook, CA (US); Richard Enoch Quintania, Fallbrook, CA (US); James Mark Cox, Winchester, CA (US); Kevin Donahue, Oceanside, CA (US)

(73) Assignee: PRYOR PRODUCTS, INC., Oceanside, CA (US)

( * ) Notice: Subject to any disclaimer, the term of this patent is extended or adjusted under 35 U.S.C. 154(b) by 0 days.

(21) Appl. No.: 16/233,703

(22) Filed: Dec. 27, 2018

(65) Prior Publication Data

US 2019/0195252 A1   Jun. 27, 2019

Related U.S. Application Data

(60) Provisional application No. 62/610,911, filed on Dec. 27, 2017, provisional application No. 62/711,389, filed on Jul. 27, 2018.

(51) Int. Cl.
| | |
|---|---|
| *F16M 13/02* | (2006.01) |
| *F16B 2/12* | (2006.01) |
| *A61M 5/14* | (2006.01) |
| *F16B 2/06* | (2006.01) |

(52) U.S. Cl.
CPC ............ *F16B 2/12* (2013.01); *A61M 5/1415* (2013.01); *F16B 2/065* (2013.01); *F16M 13/022* (2013.01); *F16M 2200/022* (2013.01)

(58) Field of Classification Search
USPC .................................................. 248/229.12
See application file for complete search history.

(56) References Cited

U.S. PATENT DOCUMENTS

| | | | | |
|---|---|---|---|---|
| 1,106,096 A | * | 8/1914 | Hunt ....................... | B25B 1/125 269/182 |
| 1,549,567 A | * | 8/1925 | Baldwin ................. | B25B 5/101 269/221 |
| 2,322,107 A | * | 6/1943 | Balcar ..................... | B25B 5/101 269/224 |
| 3,222,053 A | * | 12/1965 | Severdia .................. | B23Q 3/06 269/91 |
| 4,034,971 A | * | 7/1977 | Tsuyama ............ | B23K 37/0435 269/249 |

(Continued)

*Primary Examiner* — Monica E Millner
(74) *Attorney, Agent, or Firm* — Gordon Rees Scully Mansukhani, LLP

(57) ABSTRACT

A clamp for mounting a structure on a support. The clamp includes a fixed jaw, a base, and a moveable thruster plate between the fixed jaw and the base. The clamp includes a thruster cylinder configured to be rotatably received through the clamp body and having threads that engage a screw so that when the thruster cylinder rotates, the screw is advanced or retracted to move the thruster plate into and out of engagement with the support. A knob is used to rotate the thruster cylinder. The clamp includes a friction washer or collet located between the thruster cylinder and the clamp body. The clamp is configured so that when the thruster plate engages the support, further axial movement of the screw is prevented and further rotation of the knob and thruster cylinder compresses the friction washer or collet.

17 Claims, 6 Drawing Sheets

(56) References Cited

U.S. PATENT DOCUMENTS

| | | | | |
|---|---|---|---|---|
| 4,844,397 A * | 7/1989 | Skakoon | ............ | A61M 5/1413 248/231.71 |
| 5,326,059 A * | 7/1994 | Pryor | ............ | F16M 11/08 248/230.6 |
| 5,351,922 A * | 10/1994 | Lindsay | ............ | F16M 11/32 192/109 R |
| 5,626,320 A * | 5/1997 | Burrell | ............ | B64D 43/00 248/227.4 |
| 5,733,061 A * | 3/1998 | Child | ............ | B25B 5/101 269/249 |
| 5,779,207 A * | 7/1998 | Danby | ............ | A61M 5/1415 248/230.4 |
| 6,601,813 B1 * | 8/2003 | Kager | ............ | A45D 20/12 248/314 |
| 7,556,616 B2 * | 7/2009 | Fathallah | ............ | A61M 5/1413 604/131 |
| 7,669,816 B2 * | 3/2010 | Crain | ............ | G01C 15/00 248/183.3 |
| 8,690,507 B1 * | 4/2014 | Jesel | ............ | F16B 43/00 411/149 |
| 8,695,957 B2 * | 4/2014 | Quintania | ............ | B25B 5/006 248/309.1 |
| 9,095,946 B2 * | 8/2015 | Kotula | ............ | B25J 15/0061 |
| 9,220,821 B2 * | 12/2015 | Croizat | ............ | A61M 1/0023 |
| 9,341,308 B2 * | 5/2016 | Lacy | ............ | F16M 13/022 |
| 9,707,666 B2 * | 7/2017 | Saraie | ............ | B25B 1/10 |
| 10,365,545 B2 * | 7/2019 | Johnson, Sr. | ............ | G03B 17/561 |
| 2011/0101587 A1 * | 5/2011 | Quintania | ............ | B25B 5/006 269/74 |
| 2018/0073528 A1 * | 3/2018 | Pryor | ............ | B25B 5/06 |

\* cited by examiner

DETAIL A

COMPACT SUPPORT CLAMP

CROSS-REFERENCE TO RELATED APPLICATIONS

This application claims priority to and the benefit of U.S. Provisional Patent Application Nos. 62/610,911 filed on Dec. 27, 2017 and 62/711,389 filed on Jul. 27, 2018. The foregoing provisional patent applications are incorporated by reference herein in its entirety.

DESCRIPTION

In certain applications devices and equipment must be mounted from a support in proximity to the location where the equipment is utilized. This requirement is especially common with portable medical equipment that must be supported near where the equipment is utilized for treatment of patients.

Clamps are frequently used to mount equipment and devices to existing supports such as tubular supports as in IV poles (vertical) and bed rails (horizontal). Clamps have also been utilized with planar supports such as table edges.

A typical clamp may be a c-shaped clamp that grasps a support between a fixed jaw and a moveable jaw. The jaw operator mechanism for moving the moveable jaw into engagement with and securely grasping the support has typically utilized a screw carried in a threaded opening in the clamp body. This screw, of necessity, must be of a length greater than the maximum distance between the fixed and moveable jaws plus the width of the clamp body through which it is threaded. This creates an elongated profile that may interfere with other clamps or structures carried on the support.

Another feature which is desirable in equipment clamps is the ability to rotate attached equipment so that the equipment will be presented to the user in an upright orientation. In the past, in order to allow for the clamp to have rotational capability, projections from the clamp body have been required in order to accommodate the rotational mechanism which further increases the profile of the clamp and the potential for interference with other clamps or structures on the support.

Clamps are used to support equipment of various weights. There is a need for versatile clamps that can support heavy medical equipment. These clamps should provide secure and stable mounting and be easy and convenient to use.

The present application discloses various embodiments of clamps that include mechanisms that provide for securely mounting the clamp to a support and minimize the profile the clamp while providing versatility in view of the ever expanding size and weight of equipment being mounted. Additionally, the disclosed clamps are not solely for equipment support. The disclosed clamps may be used for clamping structural elements together.

DETAILED DESCRIPTION

Figure 1:
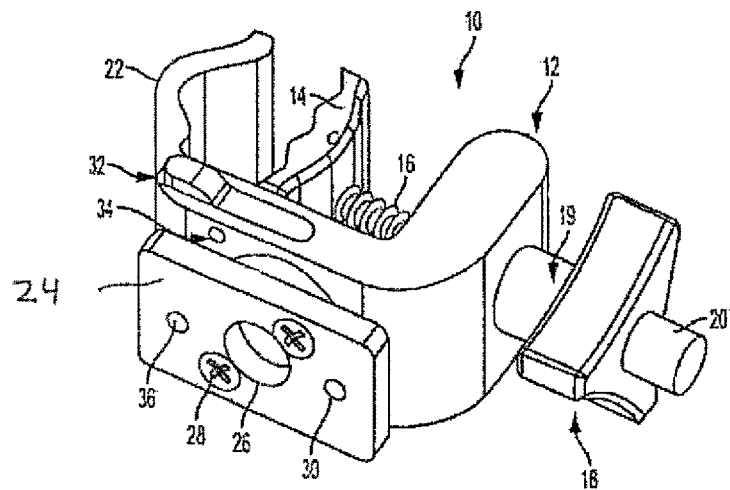
FIG. 1 is a perspective view of a clamp and mounting plate for a separate device.

In a disclosed embodiment, a compact clamp and mount is provided for attaching equipment such as medical devices to a support. The clamp is similar in concept to the clamp disclosed in U.S. patent application Ser. No. 15/427,529, which is incorporated by reference herein. The clamp incorporates a moveable thruster plate which cooperates with a fixed jaw. The clamp is capable of mounting equipment from horizontal supports (such as a table edge or bed rail) and from vertical supports (such as a movable pole for medication equipment such as IV's and IV pumps). Both cylindrical and flat supports are accommodated by shape of clamp, which includes a movable thruster plate and fixed jaw.

After the clamp is mounted on the support, the equipment may be rotated on the clamp so that the equipment is in an upright orientation. In another embodiment, dual rotational adjustment may be provided in order to allow for an adjustment to equipment such as in the vertical plane, so that the equipment may be positioned in a way that both makes it easy for the user to observe, for example, controls and displays on the equipment and at the same time avoid interference with other equipment or structures that may be carried on the same support.

The clamp body incorporates all necessary functions in a smaller space than conventional clamps. The functions that may be accommodated include indexed rotation, clamp jaw or thruster plate advance and retraction without threaded extensions outside of the clamp body, and a lock to prevent unauthorized removal of the equipment from the support, and an indexed rotation wheel.

The advance and retraction of the clamp jaw is accomplished through a thruster cylinder or barrel nut that surrounds a threaded bolt attached to the thruster. An enlarged knob is attached to the cylinder which is threaded to engage the bolt or screw near the outer end of the cylinder. The enlarged knob is sized to be easily grasped by the fingers or a user and yet provide sufficient leverage to firmly drive the thruster plate into engagement with a support. A left handed thread is provided so that clockwise rotation of the enlarged knob results in extension of the thruster plate to engage the support, which is what the user would intuitively expect from clockwise rotation.

The clamp body may optionally incorporate a lock to prevent substantial rotation of the enlarged knob and therefore prevent removal of the equipment from the support. A tubular cam lock is received in a cylindrical recess in the outer perimeter of the clamp body. A lock lever may be mounted at the inner end of the lock body. When a key is rotated to the locked position the lock lever rotates to where it is adjacent to the thruster cylinder. The cylinder mounts a nub that extends from the cylinder so that the path of the nub intersects the position of the lock lever when the enlarged knob is rotated to the locked position and limits rotation of the cylinder to less than 360 degrees. This amount of rotation is not sufficient to disengage the clamp from cylindrical or square tubing supports.

In a further disclosed embodiment, two rotational elements may be incorporated so that the position of the attached equipment may be varied to limit interference between multiple clamps attached to the same support. The second index plate may be mounted in a recess in an arm which is in turn carried on the first index plate. The arm comprises an elongated plate and has sufficient thickness to incorporate the recess for the index plate which limits the offset of the associated mount plate from the clamp body.

As shown in the figures, other embodiments of the clamp may include an assembly for improving the load capacity of the clamp. This assembly may comprise one or more collets, friction washers, and flat washers housed within an annular space located adjacent to the end of the thruster cylinder or barrel nut nearest the thruster plate. In such embodiments, the thruster cylinder may have a lip or extended edge.

Figure 12:
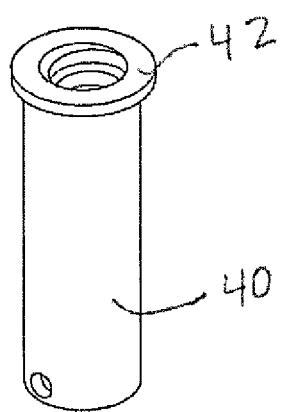
FIG. 12 is a perspective view of the thruster cylinder used in the clamps of FIGS. 3 and 8.

FIG. 1 discloses a clamp 10 with a clamp body 12. A thruster plate 14 is attached to a threaded rod, bolt or screw 16 that is advanced/retracted by operation of the enlarged knob 18 which rotates a thruster cylinder or barrel nut 40 (See FIG. 12). The thruster cylinder 40 is in threaded engagement with the screw or bolt 16. The enlarged knob 18 may include a knurled extension 20 for rapid rotation to bring the thruster plate 14 into engagement with a support (not shown) and to retract the thruster plate 14 after the tension on the support is released by use of the enlarged knob 18. The enlarged knob has a cylindrical extension 19 which surrounds the thruster cylinder and thereby provides room for the screw 16 to retract. The clamp 10 has a fixed jaw 22 opposed to the thruster plate 14.

As shown in FIG. 1, the clamp may include an optional mount plate 24. The mount plate may be secured to an index wheel 26 by fasteners 28. The mount plate incorporates two mounting bores 30 through which fasteners may be passed to secure to a piece of equipment or other structure to the clamp 10. A trigger 32 is shown received in the clamp body 12 and carried on a pivot 34. The operation of the trigger 32 and index wheel 26 is explained in greater detail U.S. patent application Ser. No. 15/427,529, which is incorporated by reference herein.

During operation of the clamp, rotation of the thruster cylinder or barrel nut 40 results in extension/retraction of the screw or bolt 16. The screw 16 does not rotate. The provision of the cylinder 40 and screw 16 provides for a compact structure that reduces the overall length profile of the clamp 10. The screw 16 extends and retracts from within the cylinder 40 so the knob 18 and does not move away from the clamp body 12 to thereby increase the effective length of the jaw. The screw 16 is preferably configured with a left-hand thread. By using a left hand thread, clockwise rotation of the knob 18 results in the advance of the clamp jaw as a user would intuitively expect and avoids the confusion that would result if a right hand thread were employed.

Because the screw 16 does not rotate, the terminus of the screw may be locked onto the jaw or plate 14. As shown in FIG. 1, the thruster plate 14 may be in the form of a waffle plate with ridges that allow the jaw to securely engage a variety of surfaces on a support such as the IV pole or to horizontal bars or planar horizontal surfaces. The waffle plate is guided by engagement with the face of the clamp body. The face of the clamp body may be flat so there is no tendency for the waffle plate to twist when it is extended toward the fixed jaw. The flats on the fixed jaw are useful for providing a substantial flat area for engaging planar surfaces.

Figure 2:
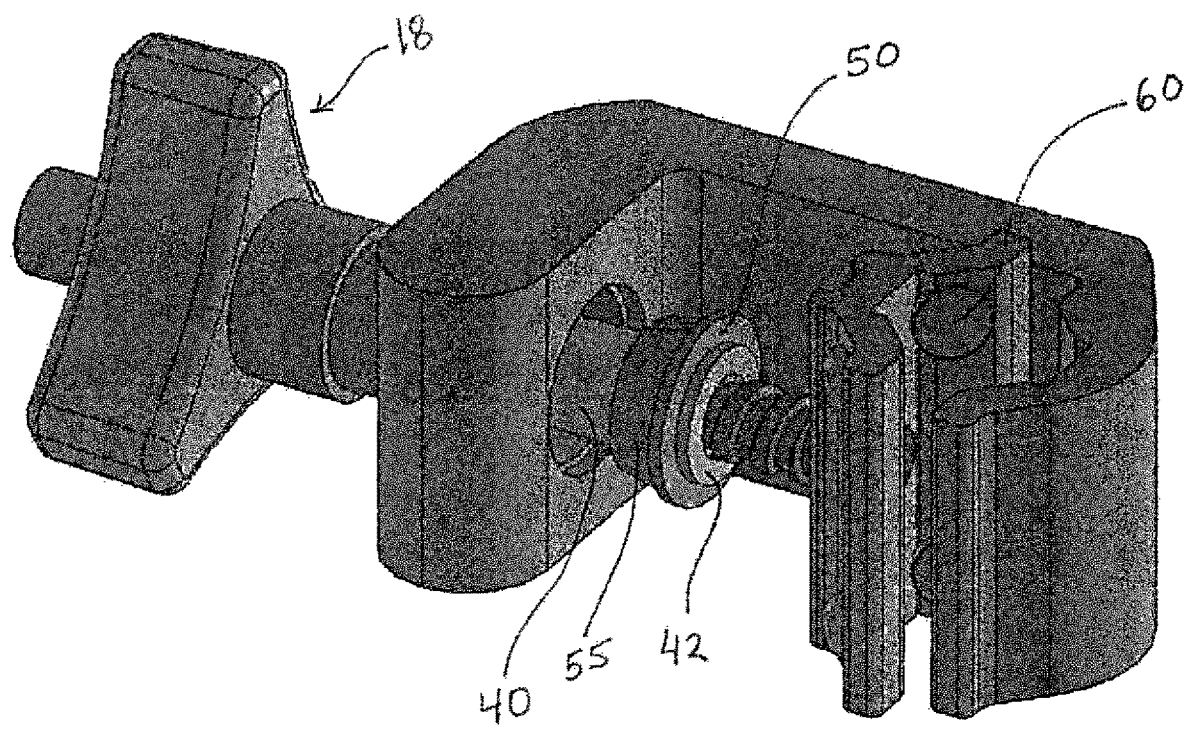
FIG. 2 is a partial exploded and perspective view of an embodiment of a clamp showing a cylindrical thruster and collet.

As shown in FIG. 2, the thruster plate 14 and/or fixed jaw 22 may be formed in a V or U shape and may include one or friction pads 60. The friction pads 60 may be formed from a rubber or plastic with a higher coefficient of friction than the remaining surface of the plate 14 or jaw 22. Alternatively, a larger area of the plate may be covered (e.g., over molded) with a suitable non-slip surface. In yet another embodiment, the entire plate 14 or fixed jaw 22 may be coated or covered with a non-slip surface.

Figure 3:
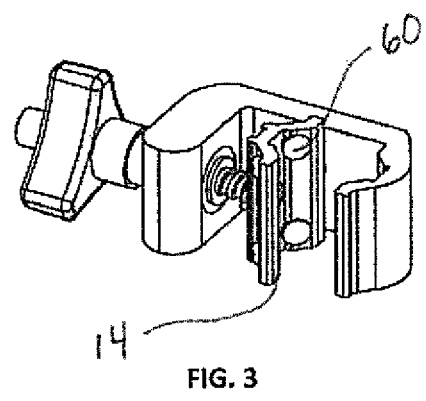
FIG. 3 is a perspective view of the assembled clamp of FIG. 2.
Figure 4:
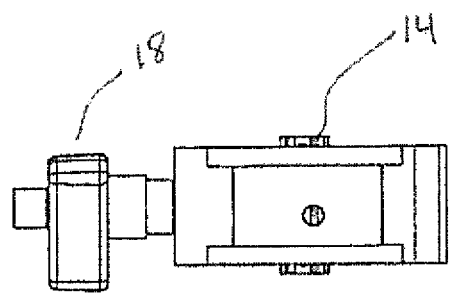
FIG. 4 is a rear view of the clamp of FIG. 3.
Figure 5:
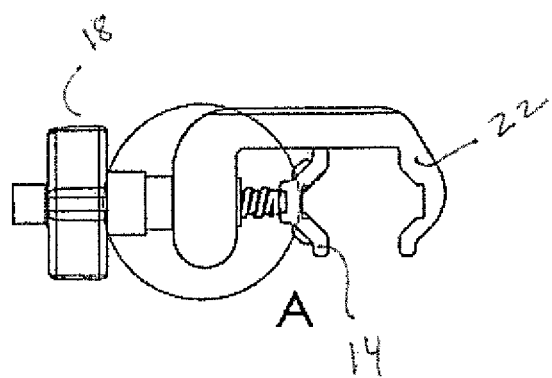
FIG. 5 is a side view of the clamp of FIG. 3.
Figure 6:
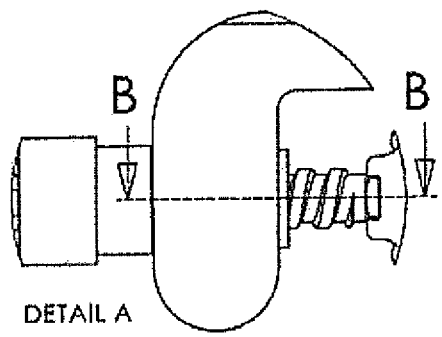
FIG. 6 is a detailed of the area of the clamp of FIG. 5 encircled and labeled as A.

FIGS. 2 and 3 show an embodiment of a clamp as described above. The clamp 10 may include a bushing located around the barrel nut 40. The bushing may take any of suitable forms to be located between the barrel nut and the clamp body. As shown in the figures, a collet 55 may be provided in an annular space within the fixed jaw of the clamp 10. The fixed jaw of the clamp includes an annular space or opening for receiving the screw 16 and the barrel nut 40. This annular space allows for the placement of one or more collets surrounding the barrel nut 40 and between the barrel nut 40 and the clamp body. A washer 50 (preferably a flat washer) is also provided between the collet 55 and the surface of the lip 42 of the barrel nut 40. The collet 55 provides for provide additional gripping force to support devices or equipment being carried by the clamp.

The collet 55 is preferably sized to have a tight fit around the circumference of the barrel nut 40. For example, the outer diameter of the barrel nut is substantially the same as the inner diameter of the collet 55. The collet 55 may be configured as a one-piece design or, alternatively, may be configured as two or more pieces that are fixed (e.g., snapped) together for ease of assembly. The outer diameter of the collet 55 may be sized to match the inner diameter of the annular and tapered opening of the clamp body. Thus, as a result, during operation of the clamp and especially when the clamp is secured against the support, the collet 55 is configured to be positioned tightly between the clamp body and the barrel nut 40.

The clamp body and associated parts are preferably formed of light-weight yet strong material. These materials may include metal (e.g., aluminum) and plastics (e.g., nylon). For example, the collet 55 may be formed of a plastic material, such as nylon. Alternatively, the collet 55 may be a molded plastic.

As with other embodiments of the disclosed clamp, advance and retraction of the thruster plate is accomplished through the barrel nut or thruster cylinder 40 that surrounds a threaded bolt or screw 16 attached to the thruster plate. In the embodiments shown in FIGS. 2-7, the thruster cylinder or barrel nut 40 includes a lip or extended edge 42 (see FIG. 12). This lip or extended edge 42 contacts the flat washer 50. A knob 18 is attached to the barrel nut. A left handed thread is provided within the cylinder so that clockwise rotation of the knob results in axial movement of the bolt and corresponding movement of the thruster plate to engage a support.

In the embodiment shown in FIGS. 2 and 3, after the thruster plate 14 has engaged the support, the knob may be further rotated. When the knob further rotates, the axial position of the bolt or screw 16 and the position of the thruster plate 14 will not change because the thruster plate has engaged the support, but the thruster cylinder 40 may continue to rotate to compress the collet 55 via the washer 50. Depending on the compressibility of the collet 55, the knob may be rotated until the washer 50 has engaged the surface of the step annular opening in the fixed jaw of the clamp. The tapered collet 55 is in contact with the barrel nut 40 and the clamp body and provides resistance to a loosening rotation of the knob and barrel nut 40. Essentially, the collet 55 provides additional force securing the thruster plate 14 in position against the support so that inadvertent contact with the knob will not disengage the thruster plate 14 from the support. A sufficient moment or torque must be applied to the knob 18 to overcome the additional frictional force being supplied by the collet 55, which is contact with the barrel nut 40 and an interior surface of the clamp body. Thus, the provision of the collet 55 provides a locking or securing function for the clamp and prevents a loosening rotation of the barrel nut 40. As a result, the disclosed clamp may support increased weight over similar clamps not provided with the clamping assembly herein disclosed. This assembly may also provide a dampening effect to the knob when loosening the clamp thereby preventing the clamp from releasing too quickly.

Figure 7:
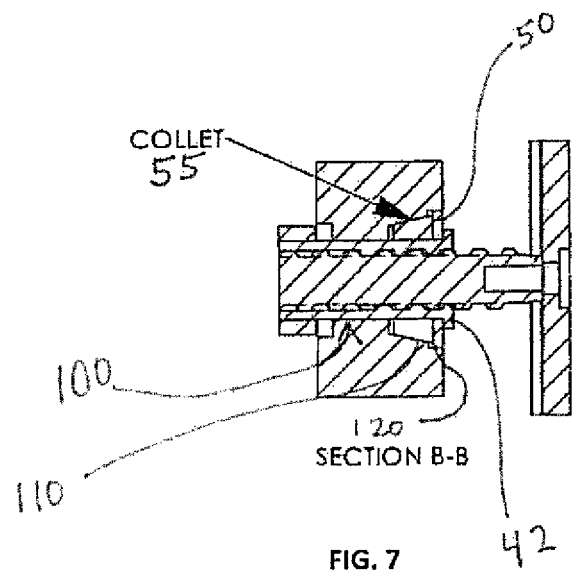
FIG. 7 is a cross-sectional view of a portion of the clamp of FIG. 5 taken along line B-B of FIG. 6.

As shown in FIG. 7, on the inner side of the fixed jaw of the clamp the annular opening includes at least three regions of differing diameter. The narrowest width or diameter section 100 is provided to accommodate the barrel nut or thruster cylinder. The largest diameter section 120 is sized to accommodate the flat washer 50. The larger diameter section extends between a shelf or ledge and the opening of the fixed jaw. The next section 110 is sized to accommodate the collet 55, and has a diameter that tapers to narrow in diameter as the opening extends away from the thruster plate 14 side of the clamp body. The base of the collet retaining section 110 of the annular opening includes a shelf or ledge that prevents axial movement of the collet 55. When the thruster cylinder moves axially toward the knob after the thruster plate 14 has engaged the support, the flat washer 50 moves with the lip of the thruster cylinder 40 to thereby contact the collet 55. The movement of the thruster cylinder is limited by the flat washer 50 contacting the ledge surface. As a result, the compressed axial length of the collet 55 may be no less than the distance between the shelf or ledge surfaces. Thus, configuration of the clamp limits excessive compression of the collet 55.

As shown in FIG. 7, on the exterior handle side of the fixed jaw of the clamp, the annular opening may include a widened section to accommodate a section of the knob 18 that may optionally protrude into the fixed jaw. As shown in the figures, the threaded screw or bolt recedes into the knob when the thruster plate is withdrawn away from the support.

An alternative embodiment of the clamp shown in FIGS. 8-11, may include a friction washer 57 instead of a collett 50. The materials properties of the friction washer allow for both compression and friction resistance when the knob is operated and, as a result, can provide for controlled release of the clamping pressure. The shape of the washer provides for an easier manufacturing for the clamp body because it is not necessary to provide a tapered opening such as used with the collet described above. For example, the opening may be easily machined using a counter bore.

FIGS. 8-11 show the alternative embodiment of the clamp as described above. The clamp 10 may include a bushing located around the barrel nut 40. The bushing may take any of suitable forms to be located between the barrel nut and the clamp body. As shown in the figures, a friction washer 57 may be provided in an annular space within the fixed jaw of the clamp 10. The fixed jaw of the clamp includes an annular space or opening for receiving the screw 16 and the barrel nut 40. This annular space allows for the placement of one or more friction washers 57 surrounding the barrel nut 40 and between the barrel nut and the clamp body. In the case of more than one friction washer, the friction washers are preferably positioned immediately adjacent to each other. A washer 50 (preferably a flat washer) is also provided between the friction washer 57 and the surface of the lip 42 of the barrel nut 40. The friction washer 57 provides for provide additional gripping force to support devices or equipment being carried by the clamp.

The friction washer 57 is sized to fit around the circumference of the barrel nut 40. The outer diameter of the friction washer 57 may be sized to match the inner diameter of the annular opening of the clamp body. Thus, as a result, during operation of the clamp and especially when the clamp is secured against the support, the friction washer 57 is configured to be positioned tightly between the clamp body and the barrel nut 40.

The clamp body and associated parts are preferably formed of light-weight yet strong material. These materials may include metal (e.g., aluminum) and plastics (e.g., nylon). For example, the friction washer 57 may be formed of a suitable non-metallic material such as, for example, urethane or vinyl. The friction washer may be formed from a compressible elastic material, such as rubber or thermoplastic material which has a relatively high coefficient of friction. Variations in washer thickness, hardness, surface area and/or coefficient of friction can vary the supplemental clamping force provided by the washer 57.

As with other embodiments of the disclosed clamp, advance and retraction of the thruster plate is accomplished through the barrel nut or thruster cylinder 40 that surrounds a threaded bolt or screw 16 attached to the thruster plate. In the embodiments shown in the application, the thruster cylinder or barrel nut 40 includes a lip or extended edge 42 (see FIG. 12). This lip or extended edge 42 contacts the flat washer 50. A knob 18 is attached to the barrel nut. A left handed thread is provided within the cylinder so that clockwise rotation of the knob results in axial movement of the bolt and corresponding movement of the thruster plate to engage a support.

In the embodiment shown in FIGS. 8-11, after the thruster plate 14 has engaged the support, the knob may be further rotated. When the knob further rotates, the axial position of the bolt or screw 16 and the position of the thruster plate 14 will not change because the thruster plate has engaged the support, but the thruster cylinder 40 may continue to rotate to compress the friction washer 57 via the washer 50. Depending on the compressibility of the friction washer 57, the knob may be rotated until the washer 50 has engaged the surface of the step annular opening in the fixed jaw of the clamp. The friction washer 57 is in contact with the barrel nut 40 and the clamp body and provides resistance to a loosening rotation of the knob and barrel nut 40.

Essentially, the friction washer 57 provides additional force securing the thruster plate 14 in position against the support so that inadvertent contact with the knob and or excessive vibration (e.g., as a result of moving over uneven surfaces) will not disengage the thruster plate 14 from the support. A sufficient moment or torque must be applied to the knob 18 to overcome the additional frictional force being supplied by the friction washer 57, which is contact with the barrel nut 40 and an interior surface of the clamp body. Thus, the provision of the friction washer 57 provides a locking or securing function for the clamp and prevents a loosening rotation of the barrel nut 40. As a result, the disclosed clamp may support increased weight over similar clamps not provided with the clamping assembly herein disclosed. This assembly may also provide a dampening effect to the knob when loosening the clamp thereby preventing the clamp from releasing too quickly.

Figure 11:
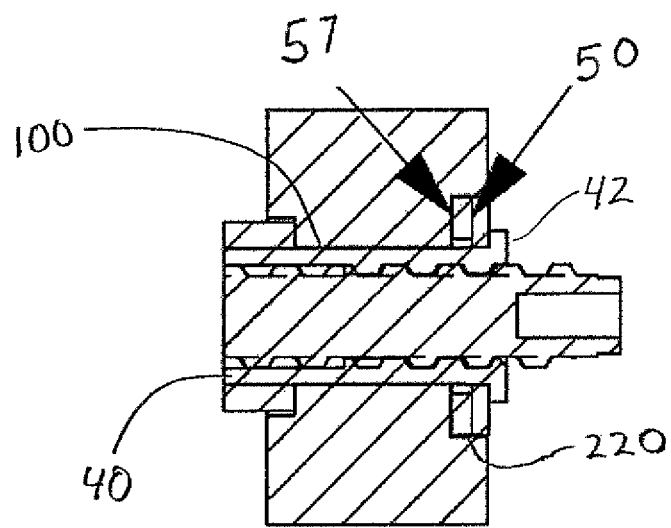
FIG. 11 is a cross-sectional view of a portion of the clamp of FIG. 8 taken along line B-B of FIG. 10.

As shown in FIG. 11, on the inner side of the fixed jaw of the clamp the annular opening includes at least two regions of differing diameter. The narrowest width or diameter section 100 is provided to accommodate the barrel nut or thruster cylinder. The largest diameter section 220 is sized to accommodate the flat washer 50 and friction washer 57. The larger diameter section extends between a shelf or ledge and the opening of the fixed jaw. When the thruster cylinder moves axially toward the knob after the thruster plate 14 has engaged the support, the flat washer 50 moves with the lip of the thruster cylinder 40 to thereby contact the friction washer 57. The movement of the thruster cylinder is limited by the friction washer 57 contacting the ledge surface, and by the compressibility of the friction washer 57.

As shown in FIG. 11, on the exterior handle side of the fixed jaw of the clamp, the annular opening may include a widened section to accommodate a section of the knob 18 that may optionally protrude into the fixed jaw. As shown in the figures, the threaded screw or bolt recedes into the knob when the thruster plate is withdrawn away from the support.

Figure 8:
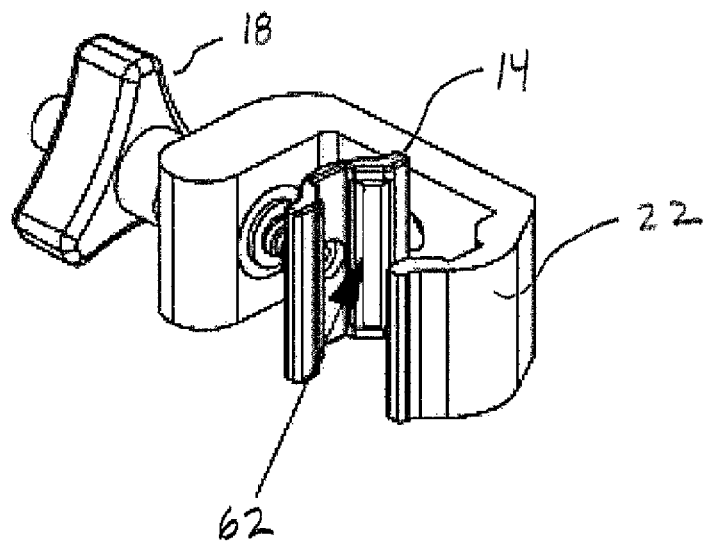
FIG. 8 is a perspective view of an embodiment of a clamp including a cylindrical thruster and friction washer.
Figure 9:
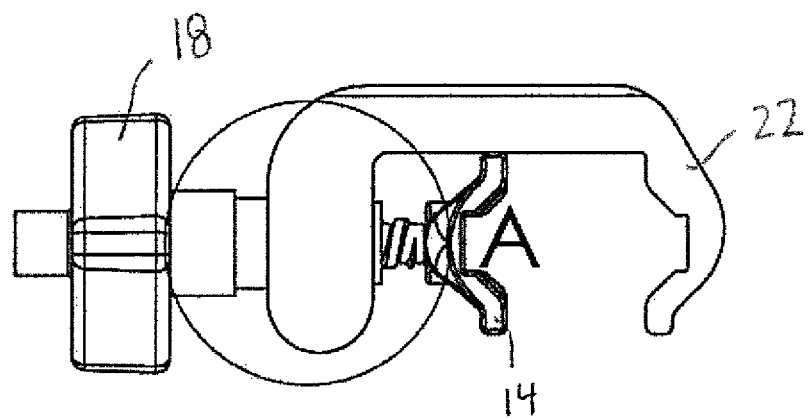
FIG. 9 is a side view of the clamp of FIG. 8.
Figure 10:
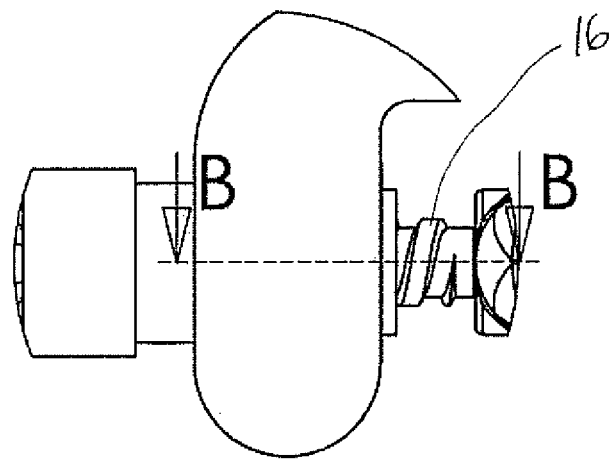
FIG. 10 is a detailed of the area of the clamp of FIG. 9 encircled and labeled as A.

Also, in the embodiment shown in FIG. 8, the thruster plate 14 and/or fixed jaw 22 may be formed in a V or U shape and may include one or friction pads 62. The friction pads 62 may be formed from a rubber or plastic with a higher coefficient of friction than the remaining surface of the plate 14 or jaw 22. Alternatively, a larger area of the plate may be covered (e.g., over molded) with a suitable non-slip surface. In yet another embodiment, the entire plate 14 or fixed jaw 22 may be coated or covered with a non-slip surface.

What is claimed:

1. A clamp for mounting and positioning a structure on a support comprising:
    a clamp body having a C-shaped profile and including
        a fixed jaw,
        a base, and
        a moveable thruster plate between the fixed jaw and the base, the thruster plate adapted to engage a support between the fixed jaw and the thruster plate; and
    a thruster cylinder configured to be rotateably received through the clamp body, the thruster cylinder having threads that engage a screw such that when the thruster cylinder is rotated the screw is advanced or retracted to move the thruster plate into and out of engagement with the support between the fixed jaw and the thruster plate; and
    a knob for rotating the thruster cylinder,
    wherein
        the base includes an annular opening storing a compressible friction washer and is configured to receive the screw and the thruster cylinder, and
        the clamp is configured so that when the thruster plate engages the support further axial movement of the screw is prevented and further rotation of the knob causes axial movement of the thruster cylinder and compression of the friction washer to thereby provide additional force securing the clamp to the support.

2. The clamp of claim 1, further comprising a flat washer located around the thruster cylinder and in the annular opening.

3. The clamp of claim 2, wherein the thruster cylinder is a barrel nut having one of a lip and an extended edge, the flat washer being adjacent to a surface of the one of the lip and the extended edge.

4. The claim of claim 3, wherein the clamp is configured so that when the thruster plate engages the support, the further rotation of the knob and the thruster cylinder causes the one of the lip and the extended edge of the thruster cylinder to apply a force to the flat washer to compress the friction washer.

5. The clamp of claim 1, further comprising a second compressible friction washer located adjacent to the first mentioned friction washer.

6. A clamp for mounting and positioning a structure on a support comprising:
    a clamp body including a fixed jaw, a base, and a moveable thruster plate between the fixed jaw and the base, wherein the thruster plate is adapted to engage a support between the fixed jaw and the thruster plate; and
    a rotateable thruster cylinder located in the clamp body, wherein the thruster cylinder includes threads that engage a screw connected to the thruster plate such that when the thruster cylinder is rotated the screw is advanced or retracted to move the thruster plate into and out of engagement with the support between the fixed jaw and the thruster plate; and
    a knob for rotating the thruster cylinder,
    a compressible friction washer located in an annular opening in the base, wherein the friction washer surrounds a base section of the thruster cylinder, and
    wherein the clamp is configured so that when the thruster plate engages the support further axial movement of the screw is prevented and further rotation of the knob causes axial movement of the thruster cylinder and compression of the friction washer by an outwardly extending lip of the thruster cylinder that overlies the friction washer to thereby provide additional force securing the clamp to the support.

7. The clamp of claim 6, wherein the clamp body is C-shaped.

8. The clamp of claim 6, further comprising a second compressible friction washer located adjacent to the first mentioned friction washer.

9. The clamp of claim 6, further comprising a flat washer located around the thruster cylinder and in the annular opening.

10. The clamp of claim 9, wherein the flat washer is adjacent to a surface of the outwardly extending lip of the thruster cylinder.

11. A clamp for mounting and positioning a structure on a support comprising:
    a clamp body having a C-shaped profile and including
        a fixed jaw,
        a base, and
        a moveable thruster plate between the fixed jaw and the base, the thruster plate adapted to engage a support between the fixed jaw and the thruster plate; and
    a thruster cylinder configured to be rotateably received through the clamp body, the thruster cylinder having threads that engage a screw such that when the thruster cylinder is rotated the screw is advanced or retracted to move the thruster plate into and out of engagement with the support between the fixed jaw and the thruster plate; and
    a knob for rotating the thruster cylinder,
    wherein
        the base includes tapered opening storing a tapered collet and is configured to receive the screw and the thruster cylinder, and the clamp is configured so that when the thruster plate engages the support further axial movement of the screw is prevented and further rotation of the knob causes axial movement of the thruster cylinder forcing the collet against the thruster cylinder and the clamp body to thereby apply additional frictional force resisting rotation of the thruster cylinder and knob.

12. The clamp of claim 11, further comprising a flat washer located around the thruster cylinder and in the annular opening.

13. The clamp of claim 12, wherein the thruster cylinder is a barrel nut having one of a lip and an extended edge, the flat washer being adjacent to a surface of the one of the lip and the extended edge.

14. The clamp of claim 13, wherein the clamp is configured so that when the thruster plate engages the support, the further rotation of the knob and the thruster cylinder causes the one of the lip and the extended edge of the thruster cylinder to apply a force to the flat washer to compress the collet.

15. The clamp of claim 1, wherein the friction washer comprises a non-metallic material.

16. The clamp of claim 6, wherein the friction washer comprises a non-metallic material.

17. The clamp of claim 11, wherein the collet comprises a plastic material.

* * * * *